United States Patent [19]

Barker et al.

[11] 4,245,517
[45] Jan. 20, 1981

[54] METHOD AND APPARATUS FOR MEASURING MODULUS OF A PLASTIC POLYMER

[75] Inventors: Robert I. Barker, Cuyahoga Falls, Ohio; Patrick F. Rice, Chesterfield, Mo.

[73] Assignee: Monsanto Company, St. Louis, Mo.

[21] Appl. No.: 1,048

[22] Filed: Jan. 5, 1979

[51] Int. Cl.³ ............................................. G01B 11/04
[52] U.S. Cl. ..................................... 73/760; 356/386
[58] Field of Search ................... 73/760, 169, 56, 55, 73/15.4; 356/384, 385, 386

[56] References Cited

U.S. PATENT DOCUMENTS

| 3,765,774 | 10/1973 | Petrohilos | 356/156 |
| 3,832,886 | 9/1974 | Pliskin | 73/56 |
| 4,037,968 | 7/1977 | King et al. | 356/386 |
| 4,061,427 | 12/1977 | Fletcher et al. | 356/159 |
| 4,096,739 | 6/1978 | Barker et al. | 73/56 |

*Primary Examiner*—Jerry W. Myracle
*Attorney, Agent, or Firm*—Gordon B. Seward

[57] ABSTRACT

The modulus of a plastic polymer is measured by extruding a strand of the polymer vertically downward through an orifice while accurately measuring the diameter of the strand, cutting off the strand and weighing it, and dividing the strand weight by the square of the difference in strand diameter to give a quotient representative of the modulus of the polymer. The method and apparatus are especially useful in measuring the green strength of a vulcanizable elastomer, so as to characterize its behavior during processing into a finished article.

5 Claims, 7 Drawing Figures

$D = T \sin \theta \left(1 - \dfrac{\cos \theta}{N(\cos \theta')}\right)$  N = REFRACTIVE INDEX OF CUBE

METHOD AND APPARATUS FOR MEASURING MODULUS OF A PLASTIC POLYMER

BACKGROUND OF THE INVENTION

The invention relates to a method and apparatus for measuring the modulus of plastic polymers, and especially of unvulcanized elastomer compounds.

The modulus of an unvulcanized elastomer compound, sometimes referred to as its "green strength", is an indication of its capacity to resist deformation in an uncured state. This property is important, for example, in the manufacture of rubber articles, when the articles are stressed before they are vulcanized. One such instance is in the manufacturing, when the components of the tire are assembled in the uncured state on a building drum, then shaped into a toroid form before final vulcanization in a mold under pressure. If the uncured compound exhibits excessive distortion under stress, certain portions of the tire may be cured in incorrect alignment with each other, and the resultant tire will be defective.

Thus, where green strength is important it is very helpful to have an accurate test for measurement of green strength, or modulus. Known techniques for measuring green strength are limited by the problems associated with applying a controlled tensile force to the sample. This is accomplished in known devices by some method of gripping the sample and then measuring its elongation under a given tensile stress. Since the polymer sample is by nature plastic, the force used in gripping it will result in distortion of the sample, with attendant inaccuracies in measurement. Similarly, known methods of measuring elongation of the sample, relying on visual observation for the most part, introduce significant errors.

Thus a need exists for a method and apparatus for quick, accurate determination of the modulus of a plastic polymer, especially an uncured vulcanizable rubber compound.

SUMMARY OF THE INVENTION

The difficulties and drawbacks associated with prior art methods and apparatus have now been solved by the instant invention, which provides a method and apparatus to measure the modulus of a plastic polymer quickly and accurately. The method involves extruding a strand of the material essentially vertically downward through an orifice, measuring the diameter of the strand at either end of a segment of the strand to give top and bottom diameter values, weighing the segment, and dividing the weight of the segment by the square of the difference between the bottom diameter value and the top diameter value to give a quotient which is representative of the modulus.

The measurement of the modulus of the plastic polymer can be accomplished by the use of the apparatus of the invention, which includes an extruder positioned so as to extrude the polymer vertically downward through an orifice so as to form a strand of the polymer, an optical measuring device positioned so as to measure the strand diameter below the orifice, a knife positioned to cut the strand below the orifice but above the measuring device, and a weighing device with a pan positioned beneath the measuring device to catch the strand and weigh it after it is severed.

When the strand of plastic polymer is extruded through the orifice and cut off below the orifice the initial diameter measurement is a maximum one, since essentially no weight of strand is present to stress the strand in tensile. As the extrusion proceeds, the increasing weight of the extruded strand results in an increasing stress, thus gradually reducing the diameter of the strand. When the strand is again cut the diameter of the top end of the strand segment is at a minimum value, having been stressed by the maximum hanging weight of the strand. This maximum hanging weight is obtained by accurately weighing the severed strand. By dividing the weight of the strand by the square of the diameter difference a quotient is obtained which is in weight units per area units, as pounds per square inch or kilograms per square centimeter. This quotient is representative of the modulus of the extrudate.

The modulus of an uncured elastomer compound is relatively low compared with that of the same compound fully cured. The method of the invention is particularly effective for uncured elastomer compounds, since it provides accurate measures of the strand diameter and of the maximum stress imposed on the strand.

Extrusion of a continuous strand of material can be accomplished using any device capable of expressing the material through an orifice or die. The Monsanto Capillary Rheometer is especially effective for this purpose, and is preferred. Its drive system is controlled so as to drive the crosshead at a constant rate independent of the loading effects of the material under test. By means of heating elements, insulation of the sample chamber and thermostatic controls the sample can be maintained at a set temperature. A pressure transducer in the barrel can provide a constant measure of the applied stress.

For measuring the diameter of the extruded strand any means may be employed which yields accurate diameter measurements. Particularly preferred for this purpose is the optical measuring apparatus disclosed and claimed in U.S. Pat. No. 4,037,968, the disclosure of which is incorporated herein by reference. This apparatus comprises a narrow beam of parallel light which scans an object which is optically located between the edges of an aperture. The light passing through the aperture is detected, and electrical signals generated proportional to the time the object interrupts the light are corrected for variations in the sweep velocity, to provide a signal representative of the width of the object independent of its position in the aperture. The strand diameter is continuously measured to provide minimum and maximum diameter values.

DESCRIPTION OF THE PREFERRED EMBODIMENTS

Figure 1:
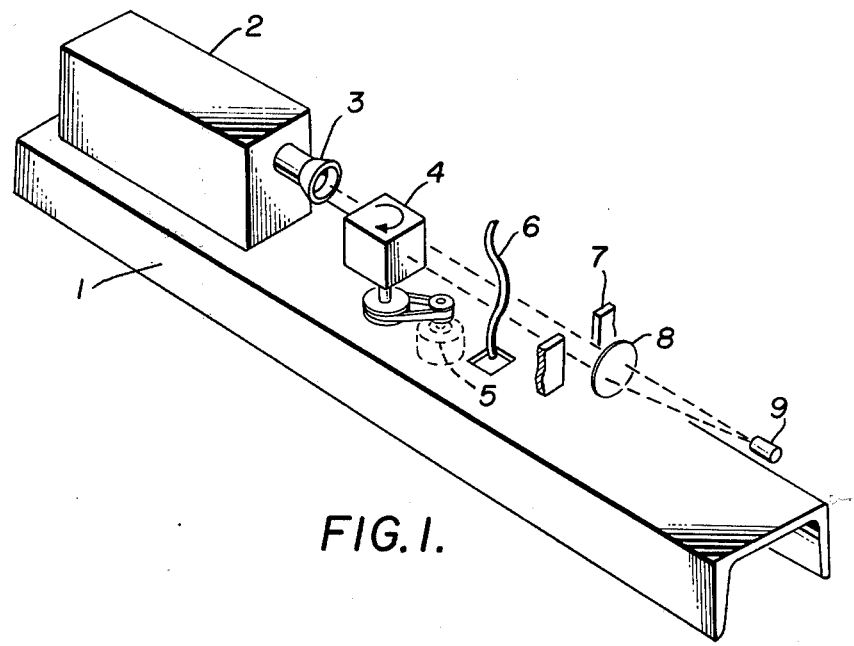
FIG. 1 is a schematic perspective view of a device for optically measuring the diameter of an extrudate strand.

Referring to FIG. 1, it shows the various elements of the optical die swell system supported by mounting frame 1. A laser 2, mounted thereon, produces a narrow beam of parallel light which is passed through a condensor/collimator 3. A cube prism 4 is rotated at substantially constant speed by motor 5. The prism maintains parallelism of the light and its rotation produces a sweep of a refrated beam of parallel light across the object 6 which in the case illustrated is continuous strand extruded from a Capillary Rheometer. The system is especially valuable for measuring small dimensions larger than can be measured by diffraction techniques and, in general, excellent results are obtainable over the range of about 0.01 inch to 1.0 inch (0.0254–2.54 cm). The beam also sweeps across measuring space 7 which is an aperture within which the strand is disposed. The aperture and, hence, the lateral active area may be 0.5 inch (1.27 cm) in a typical example but the system is not limited to this dimension. The light through the aperture passes through condensor lens 8, and the emerging beam is focused onto a photodetector 9.

Compensation for variation of position of the object within the measuring space as well as for motor speed variation is provided by a dual integration technique. To eliminate effect of motor speed variation, the electrical output (composite pulse) from the photodetector is separated into a long pulse determined by the dimensions of the aperture and a short pulse determined by the shadow of the strand or object to be measured. The long pulse starts and stops the integration of a fixed reference current from a constant current source. More particularly, the modulated current from the constant current source is gated into an aperture integrator with the long pulses created as the laser beam strikes the leading and trailing edges of the aperture. Since the aperture width is constant, the voltage output of the aperture integrator is inversely proportional to the average sweep speed of the laser beam or motor speed. Such output voltage inversely proportional to motor speed is the input to a differential amplifier which provides a current to an extrudate integrator. Because the current integrated in the extrudate integrator is inversely proportional to motor speed by the same ratio as the current integrated in the aperture integrator, the output voltage of the extrudate integrator is proportional to the strand diameter only and is not affected by motor speed. Therefore, motor speed variations have no effect on this voltage.

Figure 2:
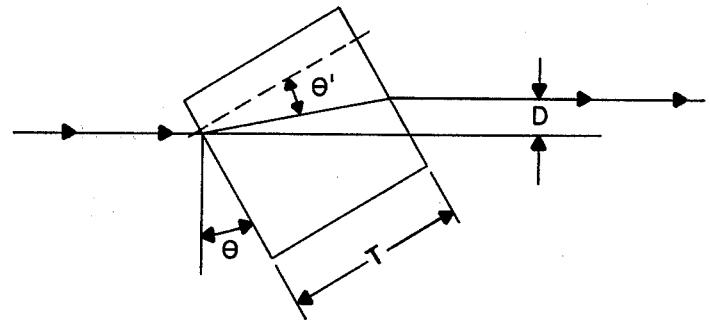
FIG. 2 is a diagram showing the displacement of a light beam caused by refraction of the light beam by a cube.
Figure 3A:
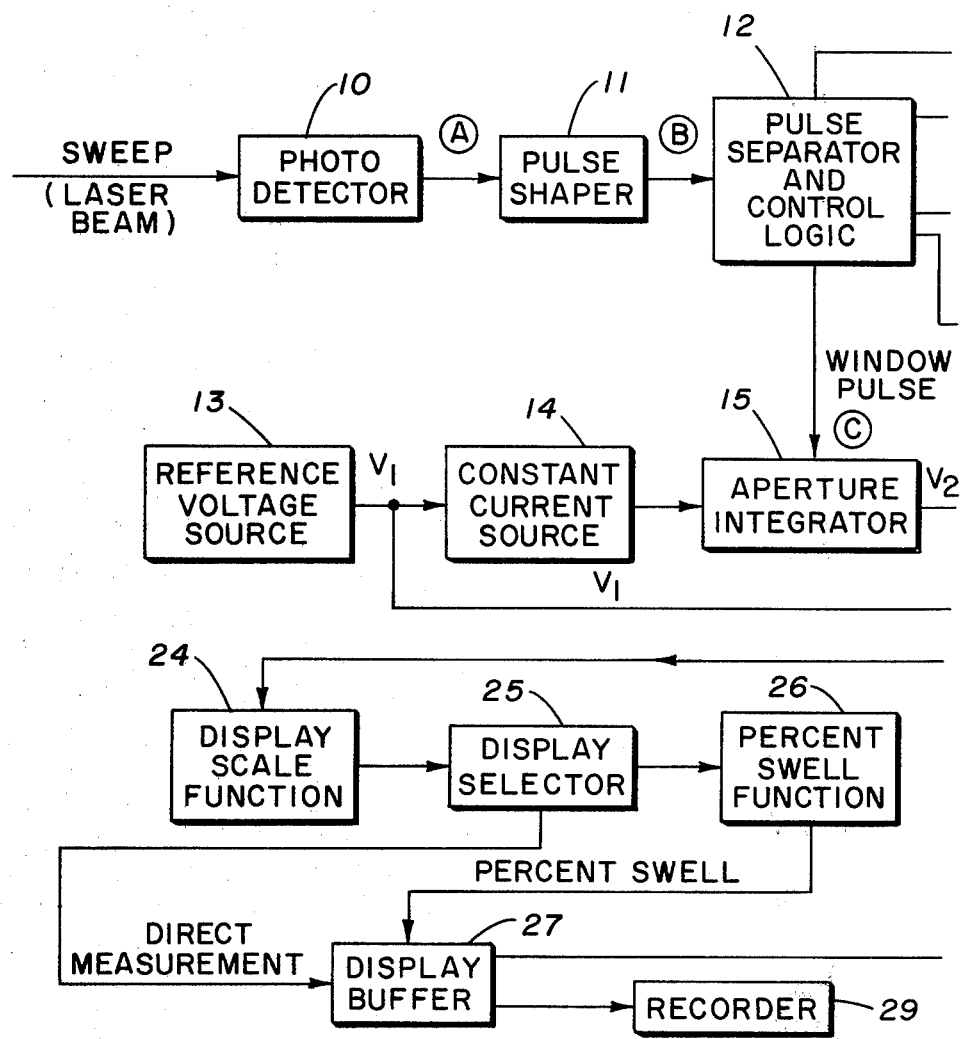
FIGS. 3a, 3b and 3c comprise a block diagram showing a preferred system for processing the light detected through the measuring space by a photo detector.
Figure 3B:
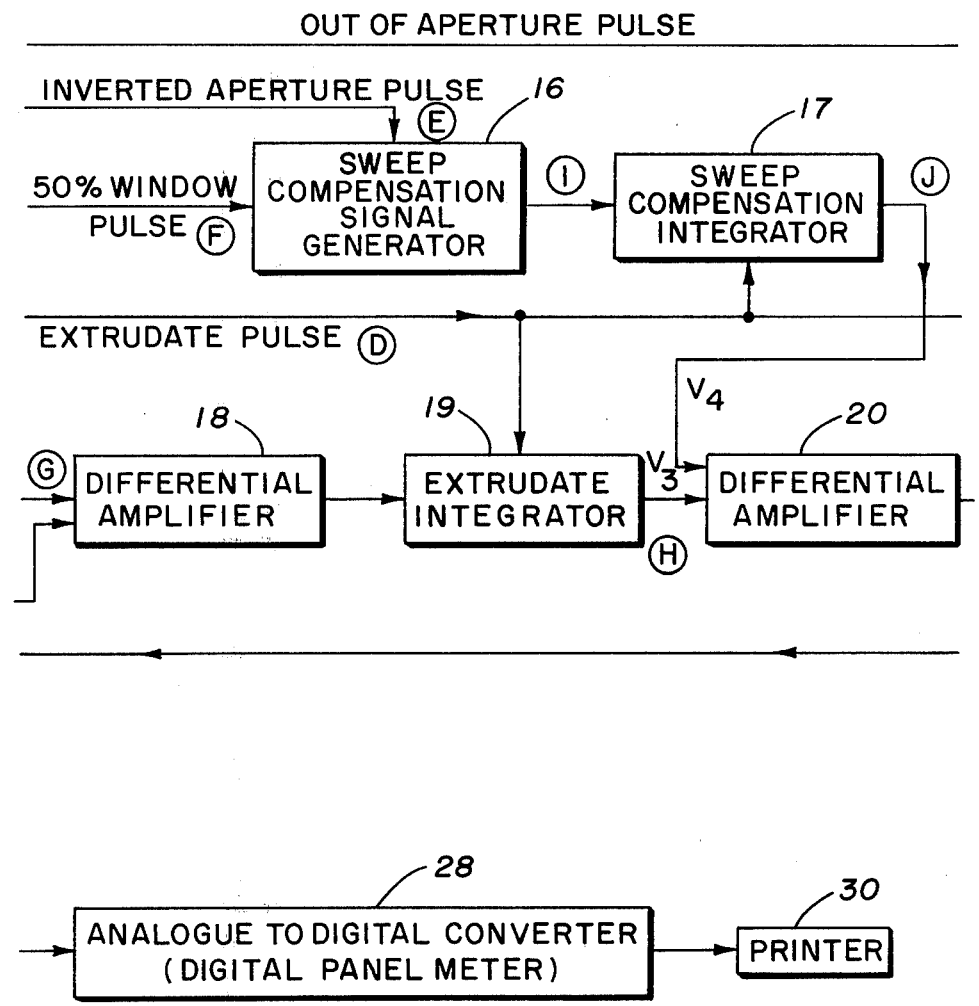
Figure 3C:
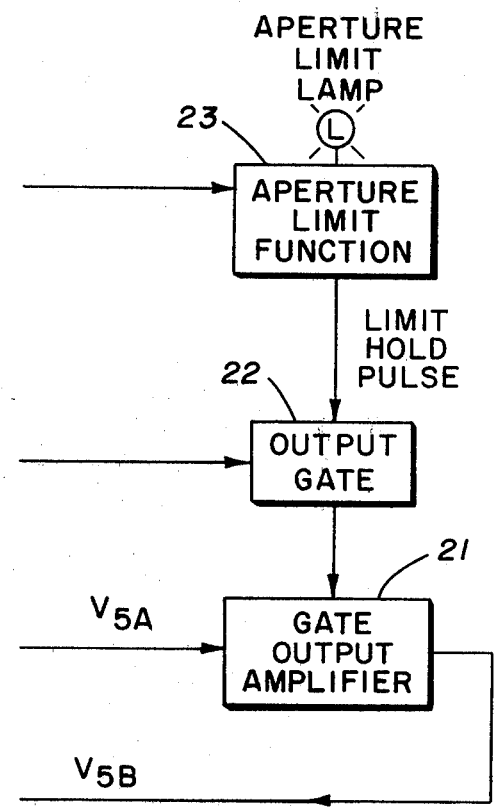

There is a geometrical velocity error created by the refraction of a light beam by a rotating cube. Refraction of a light beam by a cube creates a displacement proportional to the rotational angle of the cube as illustrated in FIG. 2. If D represents the linear displacement of the incident beam, $$D = T \sin\theta \left[ 1 - \frac{\cos\theta}{N \cos\theta'} \right]$$

where T is the length of the side of the cube, $\theta$ is the angle of incidence, $\theta'$ is the angle of deviation and N is the refractive index of the cube. The rate of change of displacement of the beam sweeping across the measuring space is not constant for a constant angular velocity but follows an approximate sine function. An approximate sine function (compensation signal) representative of rate of change of displacement of the beam is generated in synchronization with the aperture pulse from the pulse separator. This compensation signal is integrated in synchronization with a sweep compensation integrator and in synchronization with the shadow of the strand to provide offset correction for the strand integrator in relation to the position of the strand in the aperture. The outputs from the extrudate integrator and the sweep compensation integrator are summed to provide an output voltage proportional to strand diameter, which is not affected by motor speed fluctuation or position of the strand within the aperture. Effectively, the strand can move to any position in the measuring area without substantially affecting the measurement accuracy. Similarly, the strand can move in line with a receiving beam and because the spot size is constant, and the scanning beam rays are parallel, movement in this plane will not affect accuracy. The analogue voltage can then be scaled to provide dimensions in English units or metric units with a single output amplifier and panel meter.

Figure 4:
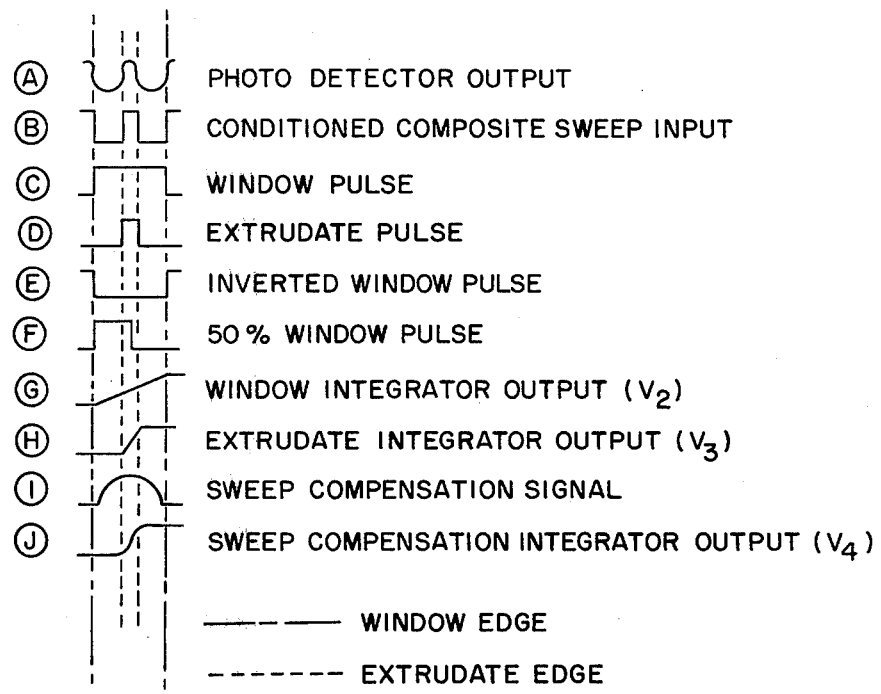
FIG. 4 is a representation of the pulse shapes involved in the system of FIG. 3.

Referring to FIGS. 3a, 3b and 3c and 4, the photodetector 10 generates a signal represented by A of FIG. 4. The illumination detected by the photodetector as the beam crosses the edge of the measuring space (aperture) from the nonilluminated to the illuminated direction rises rapidly to a maximum and then falls to a minimum again as the beam passes one edge of the strand in the illuminated to nonilluminated direction. It again rises rapidly to a maximum as the beam crosses the other edge of the strand in the nonilluminated to illuminated direction. Finally, the illumination detected by the photodetector falls once to a minimum as the beam crosses the other edge of the aperture in the illuminated to non-illuminated direction. The dashed vertical lines on FIG. 4 correspond to the aforementioned four edges.

Pulse shaper 11 converts the photoelectric output A to square pulse B so as to provide a definite low-high, high-low sequence each time the beam crosses an edge, whether it be edge of the aperture or the edge of the strand. The pulse separator and control logic 12 provide a pulse C designated "aperture pulse" representative of the width of the aperture (aperture and window are herein used synonymously) and a pulse D representative of the width of the strand designated "extrudate pulse". It follows from FIG. 2 that the sweep velocity reaches a minimum halfway between the edges of the aperture. Since the rate of change of displacement or linear velocity is greatest at the aperture edges and progressively diminishes to the center from either edge, the correction is directly proportional to distance from an edge. For synchronization it is convenient to generate an inverted aperture pulse E and a 50% aperture pulse F because the correction is symmetrical around the midpoint of the aperture.

The aperture pulse is used to start and stop the integration of a constant current 14 derived from a fixed constant voltage source 13. Since the aperture width is constant, the voltage output G of the aperture integrator 15 is inversely proportional to the average sweep speed of the laser beam determined by motor speed. This output voltage, inversely proportional to sweep speed, the supplied to one input pf differential amplifier 18. Such input ($V_2$) is compared with the reference voltage ($V_1$) from constant voltage source 13 and the algebraic sum (directly proportional to average sweep speed) supplied as the input to the extrudate integrator 19. The extrudate integrator 19 is started and stopped by the extrudate pulse D. The current is inversely proportional to sweep speed by the same ratio as the extrudate pulse width, therefore, the output of the extrudate integrator 19 is proportional to strand diameter only and not affected by average sweep speed.

A sweep compensation signal generator 16 generates a compensation signal in synchronization with the inverted aperture pulse E and the 50% aperture pulse F supplied from the pulse separator 12. This compensation signal I is integrated by the sweep compensation integrator 17 in synchronization with the extrudate pulse D. Pulse E represents the full aperture size but is inverted to afford the polarity which will enable it to perform its synchronizing function. Pulse F represents one half the aperture pulse and is used to determine the midpoint of the aperture. The leading edge of the inverted aperture pulse triggers pulse F, causing voltage to ramp up over the span of pulse F and ramp down again to zero at the end of the pulse E. The triangular wave thus formed is shaped into ½ a sine wave. When triggered by pulse F and the leading edge of the aperture, the voltage builds up at a rate approximating a sine wave function to a maximum at the point corresponding to the midpoint of the aperture then drops again to zero at the trailing edge of the aperture.

The output of the extrudate integrator 19 and the sweep compensation integrator 17, waveforms H and J, are supplied to differential amplifier 20 to be albegraically summed to provide an output voltage ($V_5A$) proportional to extrudate diameter and not affected by position of extrudate in the aperture or speed fluctuation.

The output of the differential amplifier 20 is supplied to the gated output amplifier 21, which performs a sample and hold function following each extrudate pulse D except when a limit hold pulse inhibits the output gate 22. The out of aperture pulse from the pulse separator 12 is initiated whenever the extrudate pulse D is missing in the composite pulse B input to the pulse separator 12. This condition occurs whenever the motion of the extrudate would cause it to appear (optically) to contact the edge of the aperture or to move completely out of the aperture. The out of aperture pulse triggers the aperture limit function 23 which latches into a hold condition, illuminating the aperture limit lamp L and inhibiting the output gate 22. The limit hold condition remains latched until a valid extrudate pulse appears. This latching function insures that only valid measurements are applied to display (readout) circuits.

The signal $V_5B$ from the gated output amplifier 21 is applied to the display scale function 24 which scales it in English or metric engineering units. The scaled signal from the display scale function 24 is selected by the display selector 25 for display as either direct measurement of the extrudate diameter or percent swell based upon die (orifice) diameter. The percent swell function 25 subtracts the orifice diameter from the calibrated input and converts the difference into percent swell. The output from the percent swell function 26 or the output from the display scale function is then applied to the output buffer 27 for electrical isolation and impedance matching for display devices. One output is applied to an analogue to digital converter 28 (digital panel meter) and another to recorder 29. The digital panel meter may then drive printer 30 which prints out the selected parameter in digital units. The resultant display can thus be switched at will from strand diameter, for example, in thousandths of an inch or in millimeters to percent die swell.

Although the scanning beam diameter is reduced from approximately 0.40 inches (1.016 cm) to 0.005 inches (0.0127 cm) by the condensing/collimating lens combination, there is still a potential error caused by part of the beam passing the edge of the object to be measured. Previous techniques have used a variable threshold level set for each nominal measurement or a zero crossing of the second differential of the photodetector. The former technique is effective only over a narrow range of diameters near that of a set nominal and the latter technique requires sophisticated electronics. Measurements with calibrated gauge pins have shown this beam diameter error to be a constant value for any specific beam and photodetector combination. With the above-mentioned reference integration circuit, a slight offset of the modulated reference current will effectively compensate for this beam diameter error for all diameters within the capacity of the system.

Figure 5:
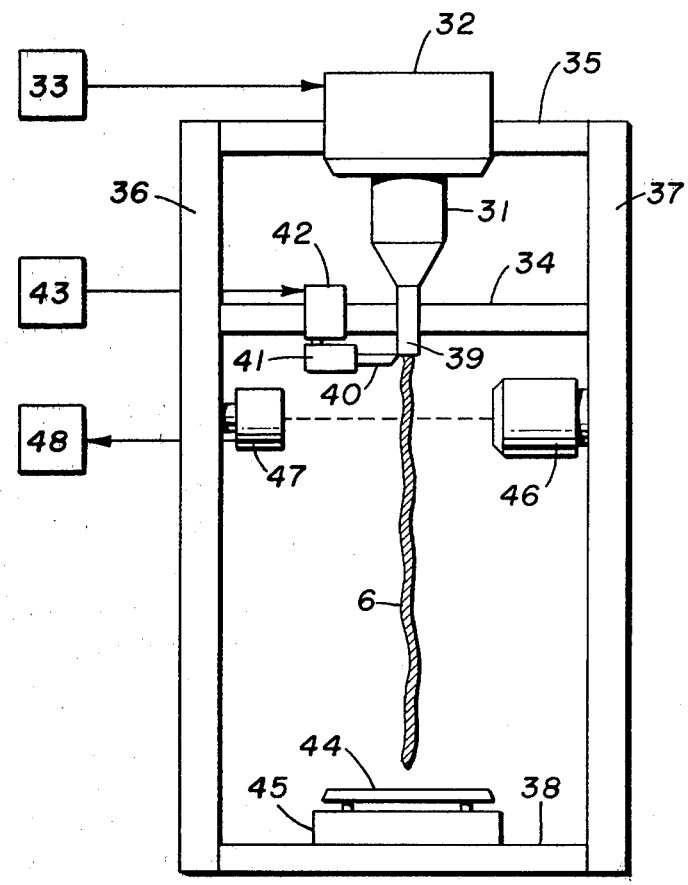
FIG. 5 is a schematic layout of a preferred device for measuring the modulus of plastic polymers.

FIG. 5 illustrates a system layout for evaluating the modulus of plastic substances by combining a capillary rheometer with the optical measuring apparatus as a strand diameter measuring device. The capillary rheometer 31 is driven by drive system 32, a closed loop servo hydraulic cylinder, controlled by digital pulses supplied by the drive electronics programmer 33. The rheometer is supported by crossmember 34, and the drive system is supported by crossmember 35, both of which are supported by vertical supports 36, 37, attached in turn to base 38.

At the orifice 39 of the rheometer, knife 40 is held by knife mount 41. Servo mechanism 42, attached to the crossmember 34 moves the knife mount 41 across the orifice so as to sever an extrudate strand 6 when actuated by control 43. The knife 40 is shown in its retracted position; when actuated it moves from left to right horizontally to sever strand 6 at the orifice 39 and allow strand 6 to fall onto pan 44. The weight of the strand 6 is transmitted to scale mechanism 45 and automatically registers on a recorder (not shown).

Laser scanning monitor 46 is the collimator rotating prism assembly previously described, and is mounted on vertical support 37. Photodetector 47 is mounted on support 36, directly opposite the laser scanning monitor 46, and views the extrudate strand 6 just below the orifice 39 and the knife 40. The photodetector 47 contains an aperture, condensing lens, and photocell, corresponding to aperture 7, condensing lens 8 and photodetector 9 of FIG. 1. Signals from photodetector 47 are relayed to strand diameter monitor electronics 48 where the diameter values are recorded and displayed.

To test an extrudable material for its modulus according to the invention, a sample of the material is first charged to the barrel of capillary rheometer 31, and brought to temperature. Extrusion of a strand through the orifice 39 of the rheometer was begun, and, after a steady flow was accomplished, the knife control 43 signaled servo mechanism 42, which actuated movement of knife 40 across the orifice 39 to sever the strand. The startup portion of the strand was then discarded.

The newly emerging strand portion 6 interrupted the laser beam emanating from the scanning monitor 46, and the resulting light pattern was picked up by the photodetector 47 and a signal was relayed to the strand diameter monitor electronics 48, where the initial diameter of strand 6 was recorded and displayed. Extrusion was continued and the strand diameter continuously measured until the bottom end of strand 6 approached, but did not contact, pan 44 of the scale mechanism 45.

At this point the servomechanism 42 was again signaled and actuated knife 40 to sever the strand again. The severed strand fell onto pan 44, and its weight was measured and recorded by scale mechanism 45. The difference between the top and bottom diameter values was obtained. By squaring this difference and dividing the strand weight by it a quotient representative of the modulus of the material was obtained.

The embodiments of the invention in which an exclusive property or privilege is claimed are defined as follows:

1. The method of measuring the modulus of an extrudable material by the steps of:
    extruding a strand of the material essentially vertically downward through an orifice,
    measuring the diameter of the strand at either end of a segment of the strand to give top and bottom diameter values,
    weighing the segment,
    and dividing the segment weight by the square of the difference between the bottom diameter value and the top diameter value to give a quotient which is representative of modulus.

2. The method of claim 1, wherein the strand diameter is optically measured.

3. The method of claim 1, wherein the extrudable material is a vulcanizable elastomer.

4. The method of claim 3, wherein the elastomer contains a vulcanizing system.

5. Apparatus for measuring the modulus of a plastic material comprising, in combination,
    extruder means to extrude a plastic material, and including an orifice; said means positioned so that a strand of plastic material can be extruded vertically downward through said orifice,
    optical measuring means capable of measuring the diameter of a strand of plastic material extruded through said orifice, said measuring means positioned so as to measure strand diameter in a horizontal plane vertically below said orifice, said measuring means capable of measuring a plurality of diameter values in said plane,
    means to cut a strand of plastic material, said means positioned above the plane of said measuring means, and
    means to weigh a strand of plastic material comprising a pan to receive a cut strand, said pan positioned below the plane of said measuring means, and beneath the orifice.

* * * * *